United States Patent [19]

Richards

[11] Patent Number: 4,927,428

[45] Date of Patent: May 22, 1990

[54] SURGICAL SUTURING SYSTEM AND PROBE ASSEMBLY

[75] Inventor: William D. Richards, Medway, Mass.

[73] Assignee: Ophthalmic Ventures Limited Partnership, Norwood, Mass.

[21] Appl. No.: 255,541

[22] Filed: Oct. 7, 1988

[51] Int. Cl.$^5$ .................. A61B 17/00; A61B 17/04
[52] U.S. Cl. ............................. 606/148; 604/902; 433/91; 227/175
[58] Field of Search ............ 128/334 R, 148; 604/35, 604/73, 129, 268, 313, 315, 902; 433/95, 91

[56] References Cited

U.S. PATENT DOCUMENTS

| | | | |
|---|---|---|---|
| 3,516,160 | 6/1970 | Leffler | 433/95 |
| 3,804,089 | 4/1974 | Bridgman | 604/902 |
| 3,916,909 | 11/1975 | Kletschka | 128/354 |
| 4,536,180 | 8/1985 | Johnson | 604/902 |
| 4,627,834 | 12/1986 | Lee | 604/902 |

FOREIGN PATENT DOCUMENTS

| | | | |
|---|---|---|---|
| 0060120 | 2/1970 | Fed. Rep. of Germany | 604/313 |
| 2611721 | 9/1977 | Fed. Rep. of Germany | 604/313 |
| 2559066 | 8/1985 | France | 604/902 |

Primary Examiner—Edward M. Coven
Assistant Examiner—Gary Jackson
Attorney, Agent, or Firm—Schiller, Pandiscio and Kusmer

[57] ABSTRACT

A surgical suturing system having a probe assembly for positioning tissue to be sutured and a stapling system for suturing tissue. The stapling system includes a stapler having a housing with a staple ejection slot, a magazine of preformed staples received within the housing and a driver for driving the leading staple in the magazine through the ejection slot. The probe assembly includes a holding probe in close proximity to the staple ejection slot, the probe assembly being adapted to connect with a vacuum source. A working end of the holding probe is configured to selectively hold onto and position the edges of the tissue to be sutured in juxtapositional coplanar alignment while the tissue is being sutured by a staple ejected from the stapler.

9 Claims, 4 Drawing Sheets

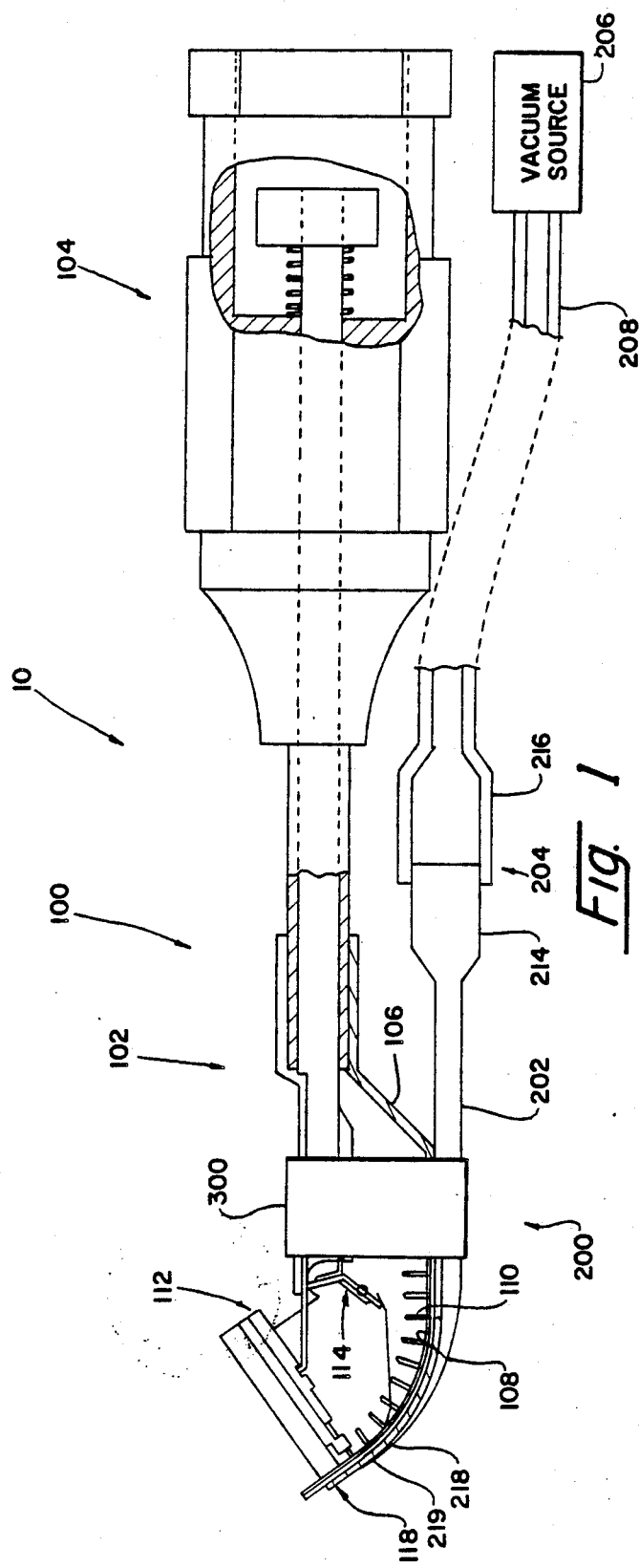
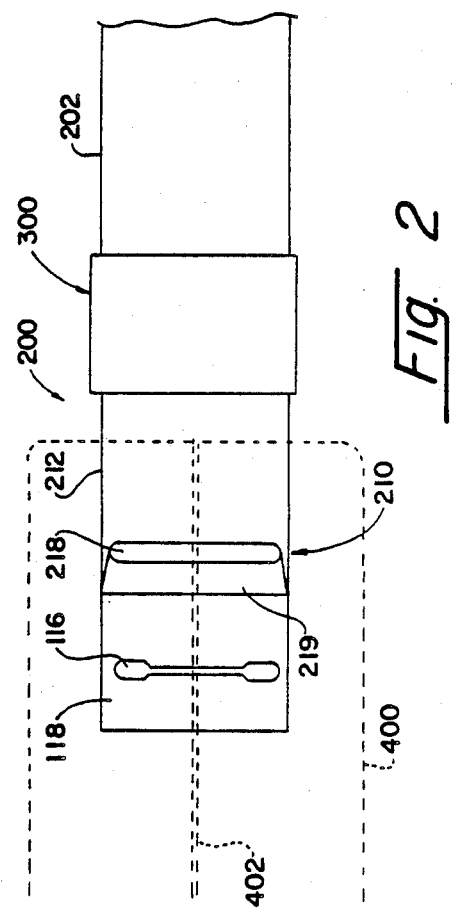

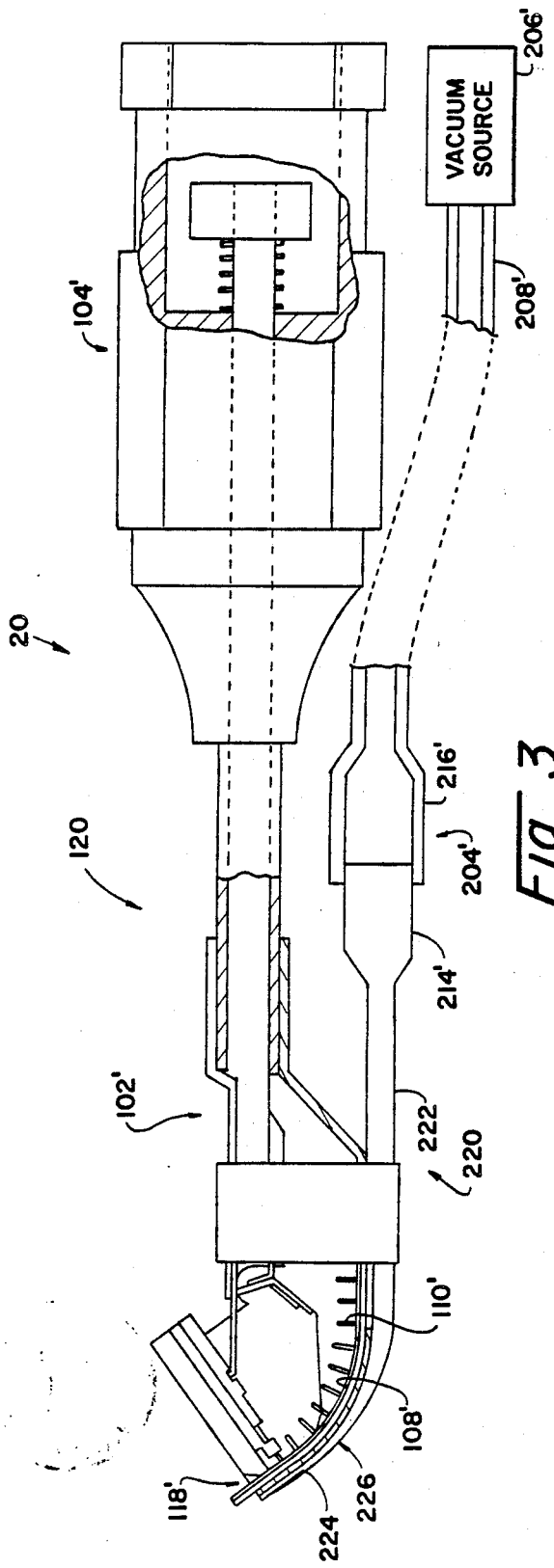
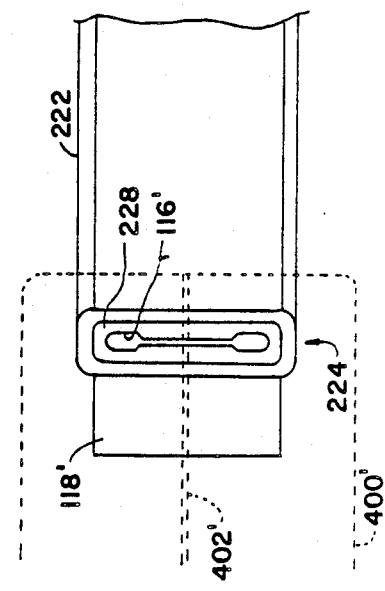
Fig. 3
Fig. 4

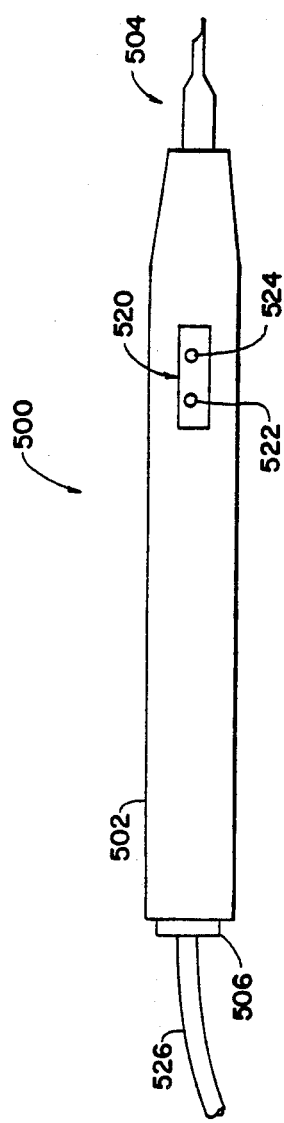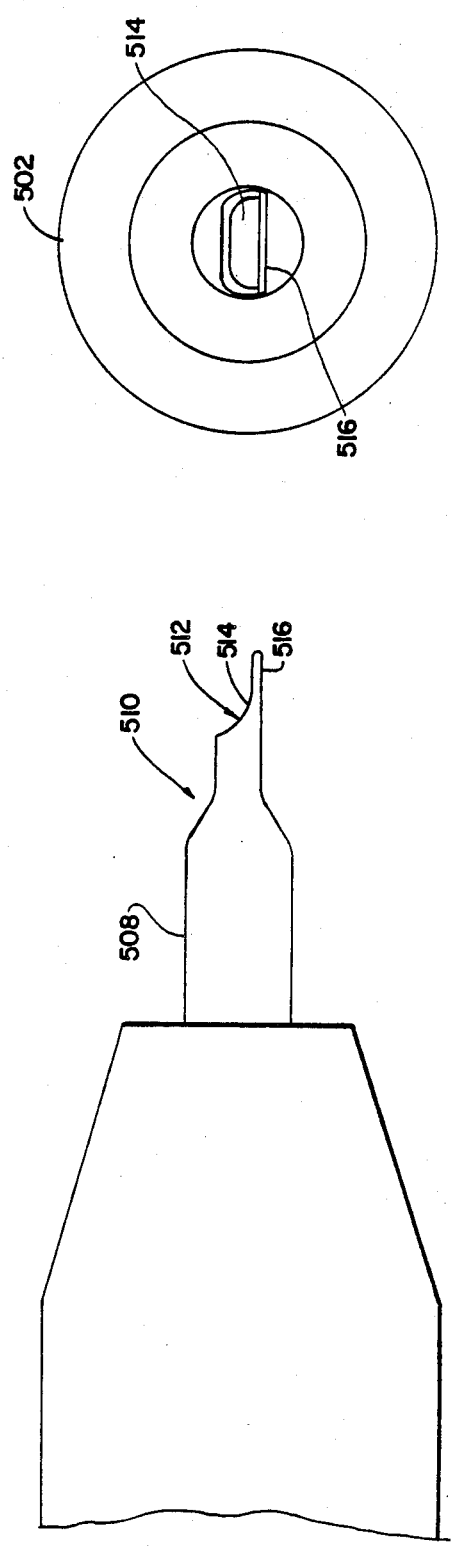
Fig. 6
Fig. 7
Fig. 8

SURGICAL SUTURING SYSTEM AND PROBE ASSEMBLY

FIELD OF THE INVENTION

The present invention relates to surgical devices used for suturing human or animal tissue and, more particularly, is directed towards a surgical suturing system and probe assembly for juxtapositioning and holding the edges of an incision in apposition during suturing.

BACKGROUND OF THE INVENTION

Suturing is a very time-consuming phase of most surgical operations. Heretofore it has been realized that suturing time can be reduced considerably by the use of stapling techniques. As a consequence, in recent years several types of stapling systems have come into use for surgical suturing.

By way of example, the following U.S. Pat. Nos. illustrate various types of staplers which have been used for suturing purposes: 3,604,561, 3,646,801, 4,162,678, 4,316,468, 4,317,451, and 4,485,816, and the references cited therein.

However, prior surgical stapling systems and probe assemblies suffer from a variety of disadvantages, including but not limited to (1) excessive size for the intended application, (2) the need to bend the staples across a stapler anvil resting on the tissue, which may induce severe traumatic effects, (3) the need to extract the stapler anvil from between the staple and the tissue surface after the staples have been implanted, and (4) the inability to maintain precise edge alignment and smoothness between opposing portions of tissue to be sutured. As a consequence, prior medical staplers have been met with varying degrees of success. A need exists for an improved surgical suturing system characterized by a device that precisely aligns the edges of the tissue to be sutured and sutures the incision.

SUMMARY OF THE INVENTION

An object of the invention is to provide a new and improved surgical suturing system which is characterized by selectively positioning and holding the edges of the tissue to be sutured in juxtapositional alignment and suturing the held edges.

Another object of the invention is to provide a probe assembly that is adapted to position and hold the edges of tissue to be sutured in juxtapositional and coplanar alignment preparatory to suturing.

Yet another object of the invention is to provide a suturing system that is adapted to position and hold the edges of the tissue to be sutured in juxtapositional alignment preparatory to suturing the tissue with staples.

A further object of the invention is to provide a surgical suturing system with a vacuum positioning system for juxtapositional alignment of the edges of an incision that is to be sutured and a staple suturing system for closing the incision.

Still another object of the present invention is to provide a suturing system for positioning and holding the edges of an incision in very delicate tissue such as the incisions involved in ophthalmic operations, neurosurgery or plastic surgery, and for suturing the incision while the edges are held in place.

Yet still another object of the invention is to provide a microsurgical stapling system in which the edges of an incision are moved into juxtapositional alignment by means of a vacuum positioning system and the edges of the incision are sutured together by means of a microstapling system which is designed to suture together delicate tissue in a manner which reduces trauma to a minimum and assures proper incision alignment, as is essential for ophthalmic or plastic surgery where incision stresses can induce post-operative deformations such as astigmatism or scarring.

These and other objects of the invention are achieved by a surgical suturing system having a probe assembly for juxtapositioning of the edges of an incision in tissue to be sutured and holding the incision edges in opposition, and a stapling system for suturing the incision in the tissue. The stapling system includes a stapler having a housing with a staple ejection slot, a magazine of preformed staples received within the housing and a driver for driving the leading staple in the magazine out the ejection slot. The probe assembly includes a holding probe disposed in close proximity to the staple ejection slot, the probe assembly being adapted to connect with a vacuum source. The probe is configured to selectively grab onto the tissue on both sides of the incision to be sutured by the stapler. In addition, the probe supports the tissue being stapled and secures the driving end of the stapler in correct driving position during deployment of the staples. In operation of the suturing system, one edge of the tissue to be sutured is held by the holding probe and moved into a position adjacent the other edge of the tissue to be sutured. Both edges are then held in juxtapositional alignment while the tissue is sutured by a staple ejected from the stapler.

The invention accordingly comprises the apparatuses and systems, together with their parts, elements and inter-relationships, that are exemplified in the following disclosure, the scope of which will be indicated in the appended claims.

BRIEF DESCRIPTION OF THE DRAWINGS

A fuller understanding of the nature and objects of the present invention will become apparent upon consideration of the following detailed description taken in connection with the accompanying drawings, wherein:

FIG. 1 is a side elevation view, partly in cross-section and partly broken away, of a surgical suturing system embodying the present invention;

FIG. 2 is an enlarged bottom plan view of the holding probe and staple ejection slot of the surgical suturing system of FIG. 1;

FIG. 3 is a side elevation view, partly in cross-section and partly broken away, of an alternative embodiment of the invention;

FIG. 4 is an enlarged bottom plan view of the holding probe and ejection slot of the surgical suturing system of FIG. 3.

FIG. 6 is a side elevation of a probe assembly embodying the invention;

FIG. 7 is a side elevation, somewhat enlarged, of the probe tip of FIG. 6; and

FIG. 8 is an end view of FIG. 7.

DETAILED DESCRIPTION OF THE PREFERRED EMBODIMENTS

Figure 5:
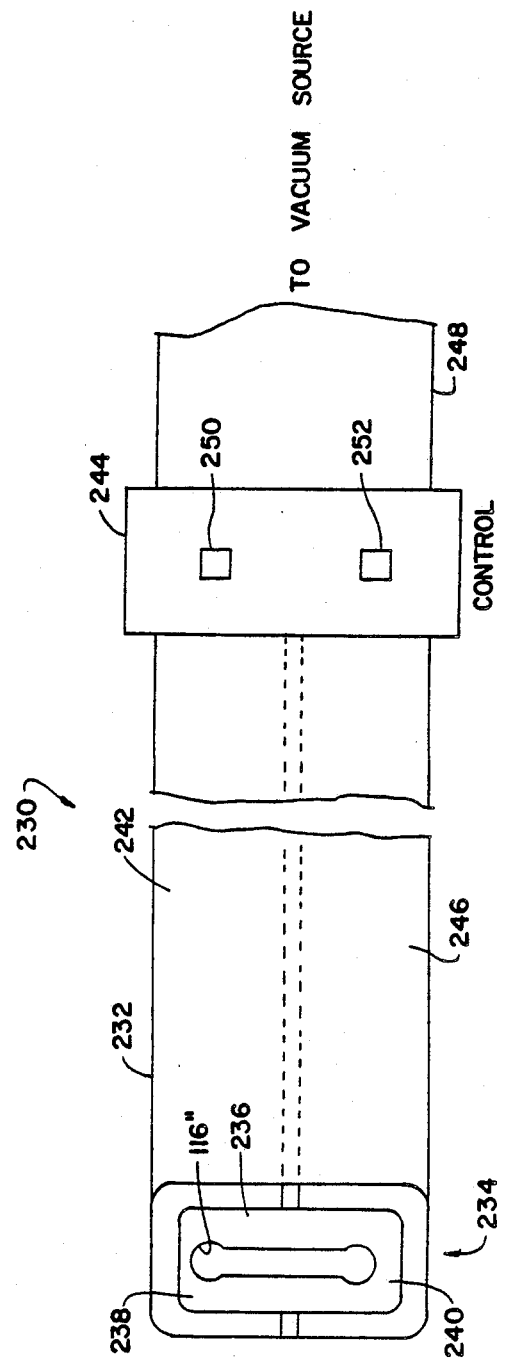
FIG. 5 is another alternative embodiment of the holding probe.

Referring now to FIGS. 1 and 2, there is shown a surgical suturing system 10 embodying the present invention. Surgical suturing system 10 includes a stapler assembly 100 and a probe assembly 200, the stapler and probe assemblies being held together by a fastener or band 300.

Stapler assembly 100 is preferably a stapler assembly of the type disclosed in U.S. patent application Ser. No. 906,151, filed Sept. 11, 1986, by Richards et al., which application is incorporated herein by reference. Alternatively, stapler assembly 100 could be another known stapler assembly capable of operating in conjunction with probe assembly 200, as will hereinafter be described in detail. Generally, stapler assembly 100 comprises a stapler 102 and an actuator 104. Stapler 102 includes a housing 106, a staple magazine 108 which contains a plurality of staples 110, a staple driver 112 and a staple advance mechanism 114. As described in the Richards et al. patent application, when actuator 104 is energized, staple driver 112 is driven downwardly toward staple magazine 108, so that staple driver 112 contacts the leading staple 110 in staple magazine 108 and the staple is ejected through an ejection slot 116 formed in the head 118 of housing 106 (FIG. 2). Staple advance mechanism 114 then advances the next staple 110 in staple magazine 108 into a position where it will be contacted by staple driver 112 and ejected from the stapler assembly 100 the next time actuator 104 is energized.

The staple 110 that is ejected through ejection slot 116 penetrates tissue 400 on opposite sides of an incision 402 (FIG. 2), the edges of the incision being moved into and held in juxtapositional alignment during the suturing process by the probe assembly 200 hereinafter described. For convenience, tissue 400 and incision 402 are shown by the dashed lines that are superimposed on probe assembly 200 in FIG. 2.

Probe assembly 200 includes a probe 202 and an interface 204 that is configured to be connected to a vacuum source 206 by means of a line 208. Probe 202 has a suction head 210 at a working end 212 and a plug 214 at an opposite end. Plug 214 is configured to interconnect with a socket 216 of interface 204.

As best shown in FIG. 2, suction head 210 terminated in a substantially oval-shaped aperture 218 and a flat tissue supporting member 219 that extends forward of the aperture. Aperture 218 is positioned in close proximity to ejection slot 116 of stapler assembly 100, tissue supporting member 219 being disposed between aperture 218 and ejection slot 116. Head 210 is used to capture and draw the edges of incision 402 into juxtapositional coplanar alignment with one another and to hold the edges of the incision in apposition while one or more staples 110 is being driven into tissue 400 to suture the tissue and close the incision. The cross-sectional area of aperture 218 is such that a vacuum is maintained at the aperture even though a portion of the aperture is holding the tissue on one side of an incision. That is, aperture 218 is sized so that a vacuum is maintained at the aperture when only a portion of the aperture is covered. The tissue to be held is pulled across the flat tissue supporting member 219 so that the tissue at the sides of the incision are held flat in coplanar relationship against the tissue supporting member. The gathering together of the edges of incision 402 and holding of tissue 400 in apposition serves many purposes, for example, it supports the tissue during suturing, secures the head 118 of stapler 102 in correct driving position for suturing the tissue, and resists relative movement between the tissue and stapler caused by stapler recoil.

In operation of surgical suturing system 10, vacuum source 206 is energized and a suction is created at aperture 218. The head 118 of stapler 102 is positioned near the edges of incision 402. The suture system 10 is rotated on its longitudinal axis and moved so that stapler head 118 approaches one edge of the incision 402. Suturing system 10 is positioned carefully and precisely so that only one edge of the incision is captured or sucked into contact with one side of aperture 218 of suction head 210. It has been found that a change in the sound emitted from vacuum source 206 is detected by the user when the tissue on one side of the incision is captured by suction head 210. The engaged edge of the incision 402 is then moved into a position beside the other or uncaptured edge of the incision. This is achieved by moving suturing system 10 (and hence its attached tissue) until the free edge of the tissue and the captured edge of the tissue are juxtaposed. Then, suturing system 10 is rotated carefully and precisely on its longitudinal axis again until the free edge of the incision is also captured by aperture 218 of suction head 210. It has been found that a further change in the sound emitted by vacuum source 206 is detected when the tissue on both sides of the incision is captured by suction head 210. Both edges of incision 402 are held in a juxtaposed coplanar relationship against flat tissue supporting member 219. Next, actuator 104 is energized and the leading staple 110 in the staple magazine 108 is driven by staple driver 112. The driven staple 110 is ejected through the ejection slot 116 and into tissue 400 for suturing the tissue and closing incision 402.

Referring now to FIGS. 3 and 4, there is shown a surgical suturing system 20 having a stapler assembly 120 and a probe assembly 220. Stapler assembly 120 is identical to the stapler assembly 100 discussed above. Accordingly, corresponding parts of stapler assemblies 100 and 120 are identified by like reference characters and distinguished by a prime notation when referring to the parts of stapler assembly 120.

Probe assembly 220 is similar to probe assembly 200 discussed above, with the exception of the relative position of the stapler ejection slot and the probe assembly's suction head, as will hereinafter be discussed in further detail. Accordingly, corresponding parts of probe assemblies 200 and 220 are identified by like reference characters and distinguished by a prime notation when referring to the parts of probe assembly 220. Probe assembly 220 includes a probe 222 and an interface 204' that is configured to be connected to a vacuum source 206' by means of a line 208'. Probe 222 has a suction head 224 at a working end 226 and a plug 214' at an opposite end. Plug 214' is configured to interconnect with a socket 216' of interface 204'.

As best shown in FIG. 4, suction head 224 is formed with an aperture 228 defining a substantially 0-shaped track. Aperture 228 is positioned about ejection slot 116' of stapler assembly 120 and defines a suction path about ejection slot 116'. As in the case of suction head 210 discussed above, head 224 is used to draw the edges of incision 402' into juxtapositional coplanar alignment with one another and hold the edges of the incision in apposition while the staple 110' is being driven into the tissue 400' for suturing the tissue and closing the incision. The gathering together of the edges of incision 402' and holding of tissue 400' in this manner supports the tissue during suturing, secures the head 118' of stapler 102' in correct driving position for suturing the tissue, and resists relative movement between the tissue and stapler caused by stapler recoil.

In operation of surgical suturing system 20, vacuum source 206' is energized and a suction is created at aperture 228. The head 118' of suturing system 20 is positioned near the edges of the incision 402'. Head 118' of the suturing system 20 is moved toward the edges of the incision 402' until one edge of the incision is captured or sucked into contact with one side of aperture 228 of suction head 224. A change in the sound emitted from vacuum source 206' indicates that tissue 400' has been captured by suction head 224. Next, the suturing system 20 is moved toward the free edge of incision 402' until the free edge is also captured by suction head 224. A further change in the sound emitted by vacuum source 206' indicates both sides of the incision are captured by vacuum probe 220. The edges of incision 402' are held in a juxtaposed coplanar relationship by suction head 224. Then, actuator 104' is energized and the leading staple 110' in the staple magazine 108' is driven through the ejection slot 116' and into tissue 400' for suturing the tissue and closing incision 402'.

Referring now to FIG. 5, there is shown a further embodiment of a probe assembly 230 made in accordance with the teachings of the present invention. Probe assembly 230 is somewhat similar to probe assembly 220 in that probe assembly 230 includes a probe 232 having a suction head 234 with an aperture 236 defining a substantially O-shaped track that is positioned about a stapler ejection slot 116, However, aperture 236 is bifurcated into a pair of substantially U-shaped tracked apertures 238 and 240 which define a bifurcated suction path. Aperture 238 is connected by a line 242 to a controller 244 and aperture 240 is connected to the controller 244 by a line 246. Controller 244 is connected to a vacuum source (not shown) by a line 248. Controller 244 includes flow controls 250 and 252 for independently controlling the suction at apertures 238 and 240, respectively.

The operation of probe assembly 230 is similar to the operation of probe assembly 220 previously described, with the exception that the suction applied to the sides of aperture 236 is independently controlled via flow controls 250 and 252. Independent control of the suction on each side of aperture 236 facilitates placement of the edges of the incision in coplanar juxtaposition alignment.

Referring now to FIGS. 6 through 8, there is shown a probe assembly 500 for positioning and holding tissue at the edges of an incision to be sutured in juxtapositional coplanar alignment preparatory to suturing. Probe assembly 500 includes an elongated body 502 having a suction head 504 at one end and a connector 506 at the other end. Suction head 504 includes a tubular member 508 that is narrowed at 510 and cut away at 512 to form a substantially oval-shaped aperture 514 with an extending flat tissue supporting member 516. The cross-sectional area of aperture 514 is sufficiently small in cross-sectional area with respect to the cross-sectional area of tubular member 504 that a suction is maintained at the aperture while only a portion of the aperture is covered by the tissue at one side of the incision to be sutured. In the illustrated embodiment, the cross-sectional area of tubular member 504 is at least one and one half times the cross-sectional area of aperture 514. A vacuum controller 520 having ports 522 and 524 is provided in body 502 for controlling the suction at aperture 514.

Suction head 504 is used to capture and draw the tissue at the edges of an incision into juxtapositional coplanar alignment with one another and hold the tissue in apposition while the incision is being sutured by surgical staples or conventional suturing or other means for closing an incision.

In operation of probe assembly 500, a vacuum source (not shown) is connected to probe assembly 500 by means of a line 526 that is fitted to connector 506. Aperture 514 is positioned adjacent the tissue at one edge of the incision and port 522 is covered to increase the suction at aperture 514. The suction pulls the tissue at the one side of the incision across a portion of tissue supporting member 516 and covers a portion of aperture 514. Next, the captured tissue is moved to close the incision and the suction pulls the tissue at the other side of the incision across tissue supporting member 516 and aperture 514. Port 524 is then covered to further increase the hold on the tissue so that the tissue will be securely supported during subsequent incision closing. The two pieces of tissue are held in juxtapositional coplanar alignment while the incision is closed by stapling, conventional suturing or other incision closing means.

Since certain changes may be made in the foregoing disclosure without departing from the scope of the invention herein involved, it is intended that all matter contained in the above description and depicted in the accompanying drawings be construed in an illustrative and not in a limiting sense.

What is claimed is:

1. A probe assembly for positioning and holding human and animal tissue for suturing, the probe assembly comprising an elongated body having a hollow interior, a narrowed working end, and a rear end, said working end including (a) a suction head having a long, narrow slot coupling said interior of said body with the region outside said body, said slot being positioned so that an axis extending along the long dimension of the slot extends perpendicular to the elongate axis of said body, and (b) a flat supporting member positioned forward of said slot, said rear end comprising an opening and being adapted for attachment to a vacuum source so as to couple said hollow interior with said vacuum source.

2. A probe assembly as claimed in claim 1 wherein the cross-sectional area of said hollow interior of said body is at least one and one half times the cross-sectional area of said slot.

3. A probe assembly as claimed in claim 1 including control means operatively connected to said body for regulating the suction at said slot.

4. A probe assembly as claimed in claim 1 including at least two port means formed in said body for regulating the suction at said slot.

5. A probe assembly according to claim 1, further wherein said elongate body comprises means for separating said hollow interior into first and second suction paths, said first suction path being constructed to couple a first side of said slot with said opening in said rear end and said second suction path being constructed to couple a second side of said slot with said opening in said rear end.

6. A probe assembly according to claim 5 wherein said probe further comprises first control means for regulating the suction in said first suction path and second control means for regulating the suction in said second suction path.

7. A method of positioning and holding the edges of tissue to be sutured in juxtapositional and coplanar alignment preparatory to suturing the tissue, the method comprising in sequence the steps of:

providing a vacuum positioning apparatus comprising an elongate tubular member having a hollow interior, a narrowed working end and a rear end, said member including (a) an elongate aperture coupling said interior with an atmosphere outside said member, said aperture being positioned so that the axis extending along the elongate dimension thereof extends perpendicular to the long axis of said member, and (b) a flat supporting member attached to said working end adjacent said aperture, said rear end being adapted for attachment to a vacuum source so as to couple said interior with said vacuum source;

attaching said rear end to a vacuum source and operating said vacuum source so as to create a suction at said aperture;

positioning said working end adjacent an incision in tissue and then manipulating said tubular member so that tissue on one side of said incision is drawn into contact with one side of said aperture and one side of said flat supporting member by the suction provided at said aperture;

manipulating said tubular member so as to cause said tissue confronting said one side of said incision to move into juxtapositional relationship with tissue on the other side of said incisions; and manipulating said tubular member so as to cause said tissue on said other side of said incision to be drawn into contact with the other side of said aperture and the other side of said flat supporting member by the suction provided at said aperture.

8. A method according to claim 7 wherein said vacuum source is operated so that said suction at said aperture is of sufficient strength to hold said tissue drawn into contact with said aperture and said flat supporting member against said aperture and flat supporting member while said tissue is being sutured.

9. A method according to claim 7 wherein said vacuum source is operated so that a suction is maintained at said aperture even when only a portion of said aperture is covered by said tissue.

* * * * *